US009572741B2

United States Patent
Weaver et al.

(10) Patent No.: US 9,572,741 B2
(45) Date of Patent: Feb. 21, 2017

(54) SURGICAL TABLE ARM SUPPORT ASSEMBLY AND SURGICAL TABLE

(71) Applicant: TIDI CFI Products, LLC, Fenton, MI (US)

(72) Inventors: Greg Weaver, Sherman Oaks, CA (US); James H. Niedzielski, Fenton, MI (US)

(73) Assignee: TIDI CFI Products, LLC, Fenton, MI (US)

( * ) Notice: Subject to any disclaimer, the term of this patent is extended or adjusted under 35 U.S.C. 154(b) by 96 days.

(21) Appl. No.: 14/471,690

(22) Filed: Aug. 28, 2014

(65) Prior Publication Data
US 2015/0059097 A1    Mar. 5, 2015

Related U.S. Application Data

(60) Provisional application No. 61/871,100, filed on Aug. 28, 2013.

(51) Int. Cl.
| | |
|---|---|
| *A61G 13/12* | (2006.01) |
| *A61G 7/075* | (2006.01) |
| *A47C 20/02* | (2006.01) |
| *A61F 5/37* | (2006.01) |
| *A61G 13/00* | (2006.01) |

(Continued)

(52) U.S. Cl.
CPC ......... *A61G 13/1235* (2013.01); *A47C 20/023* (2013.01); *A61F 5/3723* (2013.01); *A61G 7/075* (2013.01); *A61G 13/0036* (2013.01); *A61G 7/0503* (2013.01); *A61G 13/101* (2013.01); *A61G 13/1285* (2013.01)

(58) Field of Classification Search
CPC  A61G 13/12; A61G 13/1205; A61G 13/1235; A61G 13/124; A61G 13/126; A61G 13/1285; A61G 7/075; A61G 7/0503; A61G 13/0036; A61G 13/101; A61F 5/37; A61F 5/3715; A61F 5/3723; A61F 5/3769; A47C 20/023
See application file for complete search history.

(56) References Cited

U.S. PATENT DOCUMENTS

| 490,541 A | * | 1/1893 | Case | ........................ | A47C 7/38 |
| | | | | | 297/405 |
| 1,516,795 A | * | 11/1924 | Schwarting | ............ | A61G 13/12 |
| | | | | | 248/118 |

(Continued)

*Primary Examiner* — Nicholas Polito
*Assistant Examiner* — David R Hare
(74) *Attorney, Agent, or Firm* — Boyle Fredrickson, S.C.

(57) ABSTRACT

A surgical table arm support assembly and surgical table therewith is provided. The assembly includes a mount bracket and an upright support member operably attached to the mount bracket. A lateral support member is operably attached to the upright support member. The lateral support member is selectively movable about 3 axes. An arm support member is operably attached to the lateral support member. The arm support member is selectively movable about 3-axes. The arm support member can be precisely positioned and releasably fixed in the desired position to best assure the patient's arm, which is releasably fixed to the arm support member, is properly supported and located over the course of a lengthy surgical procedure to minimize the risk of trauma resulting from the arm being supported in a rearward extending, elevated position.

14 Claims, 8 Drawing Sheets

(51) Int. Cl.
  *A61G 7/05* (2006.01)
  *A61G 13/10* (2006.01)

(56) References Cited

U.S. PATENT DOCUMENTS

| | | | | |
|---|---|---|---|---|
| 1,887,022 A | * | 11/1932 | Hoffman | A61F 5/3715 128/877 |
| 2,119,325 A | * | 5/1938 | Goodhart | A61M 5/52 248/118 |
| 2,459,033 A | | 1/1949 | Kraus | |
| 2,658,211 A | * | 11/1953 | Bendersky | A61G 7/075 5/623 |
| 2,766,463 A | * | 10/1956 | Bendersky | A61G 7/075 248/118 |
| 3,046,072 A | * | 7/1962 | Douglass, Jr. | A61G 13/12 5/623 |
| 3,910,538 A | * | 10/1975 | Baitella | F16M 11/14 248/124.1 |
| 4,708,510 A | * | 11/1987 | McConnell | A61G 13/12 403/137 |
| 5,135,210 A | * | 8/1992 | Michelson | A61G 13/12 5/623 |
| 5,263,497 A | * | 11/1993 | Grabenkort | A61B 5/0084 128/869 |
| 5,281,001 A | * | 1/1994 | Bergsten | A47B 21/0371 248/118 |
| 5,407,249 A | * | 4/1995 | Bonutti | A47B 21/0371 248/118 |
| 5,582,379 A | * | 12/1996 | Keselman | A61F 5/3761 248/229.25 |
| 6,022,079 A | * | 2/2000 | Bergsten | A47B 21/0371 297/411.35 |
| 6,203,109 B1 | * | 3/2001 | Bergsten | A47B 21/0371 297/411.35 |
| 6,554,364 B1 | * | 4/2003 | Dammermann | A47C 1/03 297/411.35 |
| 6,619,598 B2 | * | 9/2003 | De Miranda | A61B 90/60 248/118.3 |
| 6,663,055 B2 | * | 12/2003 | Boucher | A61G 13/12 248/118 |
| 7,055,910 B2 | * | 6/2006 | Wright | A61F 5/3761 297/411.23 |
| 7,862,123 B2 | * | 1/2011 | Baker | A47C 7/54 297/115 |
| 8,106,278 B2 | * | 1/2012 | Eason | F16B 12/40 403/90 |
| 8,656,536 B1 | * | 2/2014 | Sorg | A61G 13/1205 378/209 |
| 2002/0128577 A1 | * | 9/2002 | Smart | A61F 5/04 602/36 |
| 2005/0251076 A1 | | 11/2005 | Branch | |
| 2008/0172791 A1 | | 7/2008 | Walczyk | |
| 2010/0018537 A1 | | 1/2010 | Soto et al. | |

\* cited by examiner

SURGICAL TABLE ARM SUPPORT ASSEMBLY AND SURGICAL TABLE

CROSS-REFERENCE TO RELATED APPLICATION

This application claims the benefit of U.S. Provisional Application Ser. No. 61/871,100, filed Aug. 28, 2013, which is incorporated herein by reference in its entirety.

BACKGROUND OF THE INVENTION

1. Technical Field

This invention relates generally to surgical devices, and more particularly to surgical table arm supports.

2. Related Art

During surgery on a patient's upper body or neck region, such as when a surgeon needs to gain access to the patient's jugular vein, for example, sometimes the surgeon needs to position the patient's arm upwardly so that the arm extends above their head. Typically, the surgeon elevates the patient's arm by supporting the forearm region on one or more pillows or folded blankets. Unfortunately, the pillows, blankets, or the like do not offer the ability to precisely position the patient's arm, and thus, the position attained may be less than optimal for both the surgeon as well as the patient. Further, using such devices to position the patient's arm offers little assurance the arm will remain "as positioned", particularly if the supporting device shifts or becomes inadvertently dislodged. If the patient's arm is or becomes improperly positioned, trauma can be caused to the patient, and most commonly, the brachial plexus nerve bundle can be temporarily or permanently damaged.

SUMMARY OF THE INVENTION

In accordance with one aspect of the invention, a surgical table arm support assembly is provided. The assembly includes a mount bracket and an upright support member operably attached to the mount bracket. A lateral support member is operably attached to the upright support member. The lateral support member is selectively movable about 3 axes. An arm support member is operably attached to the lateral support member. The arm support member is selectively movable about 3-axes. Accordingly, the arm support member can be precisely positioned and fixed in the desired position to assure the patient's arm, which is releasably fixed to the arm support member, is properly supported and located over the course of a lengthy surgical procedure to minimize the risk of trauma resulting from the arm being positioned in an elevated position on the arm support member for an extended period of time, including hours.

In accordance with another aspect of the invention, the surgical table arm support assembly can include a single lever configured to simultaneously lock and release the lateral support member and the arm support member relative to one another and relative to the mount bracket and upright support member.

In accordance with another aspect of the invention, the surgical table arm support assembly can further include a line guide member operably attached to the mount bracket, wherein the line guide member preferably has a plurality of support regions for releasably retaining lines in a fixed location to avoid the lines from interfering with one another and with the surgical team.

In accordance with another aspect of the invention, the arm support member can include a rigid support plate and a separate compliant arm pad releasably fixed to the rigid support plate, thereby facilitating cleaning the separate components and customization of the arm pad.

In accordance with another aspect of the invention, the mount plate can have one of protrusions or recessed pockets and the rigid support plate can have the other of the protrusions or recessed pockets, wherein the recessed pockets are aligned to slidingly receive the protrusions in ratcheting fashion to selectively maintain the arm support in a releasably fixed position.

In accordance with another aspect of the invention, a combination of a surgical table arm support assembly and surgical table having an upper patient support surface is provided. The surgical table arm support assembly includes a mount bracket operably attached to the surgical table. An upright support member is operably attached to the mount bracket. The upright support member extends upwardly from the upper patient support surface of the surgical table. A lateral support member is operably attached to the upright support member. The lateral support member extends laterally from the upright support member and is movable about 3 axes. An arm support member is operably attached to the lateral support member in cantilevered relation with the lateral support member. The arm support member extends laterally away from the upright support member and is movable about 3-axes.

In accordance with another aspect of the combination, the surgical table arm support assembly can further include a single lever operable to simultaneously lock the lateral support member, the arm support member, and the lateral support member against relative movement with one another, and to simultaneously release the lateral support member, the arm support member, and the upright support member for relative movement with one another.

In accordance with another aspect of the combination, the surgical table arm support assembly can further include a line guide member operably attached to the mount bracket, with the line guide member having a plurality of slots for releasably retaining lines in a fixed position.

In accordance with another aspect of the combination, the arm support member is moveable telescopically relative to the lateral support member.

BRIEF DESCRIPTION OF THE DRAWINGS

These and other aspects, features and advantages of the present invention will become more readily appreciated when considered in connection with the following detailed description of presently preferred embodiments and best mode, appended claims and accompanying drawings, in which:

DETAILED DESCRIPTION OF PRESENTLY PREFERRED EMBODIMENTS

Figure 1:
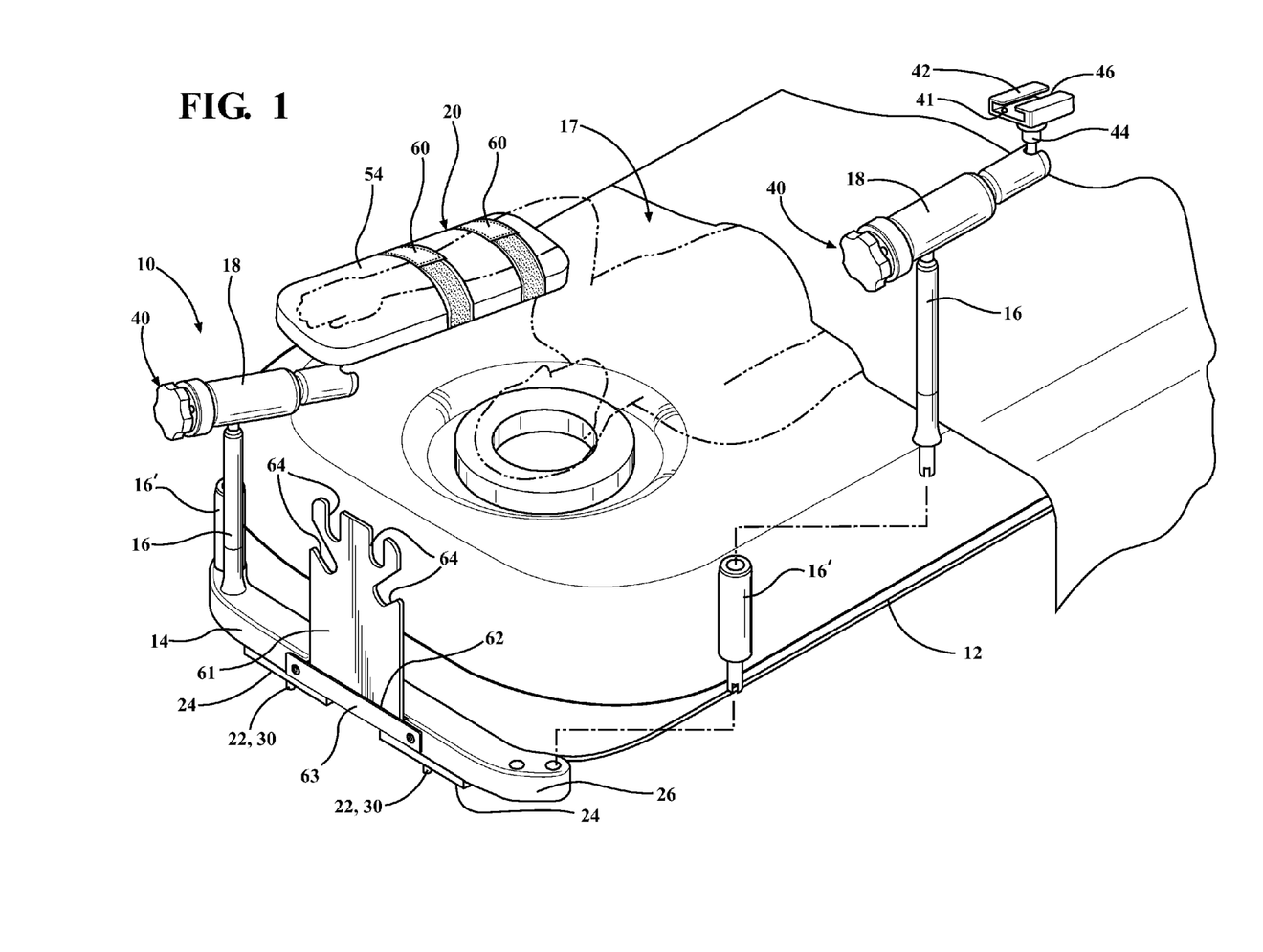
FIG. 1 is a partial perspective view of a surgical table with a surgical table arm support assembly constructed in accordance with one aspect of the invention supporting a patient's arm.
Figure 2A:
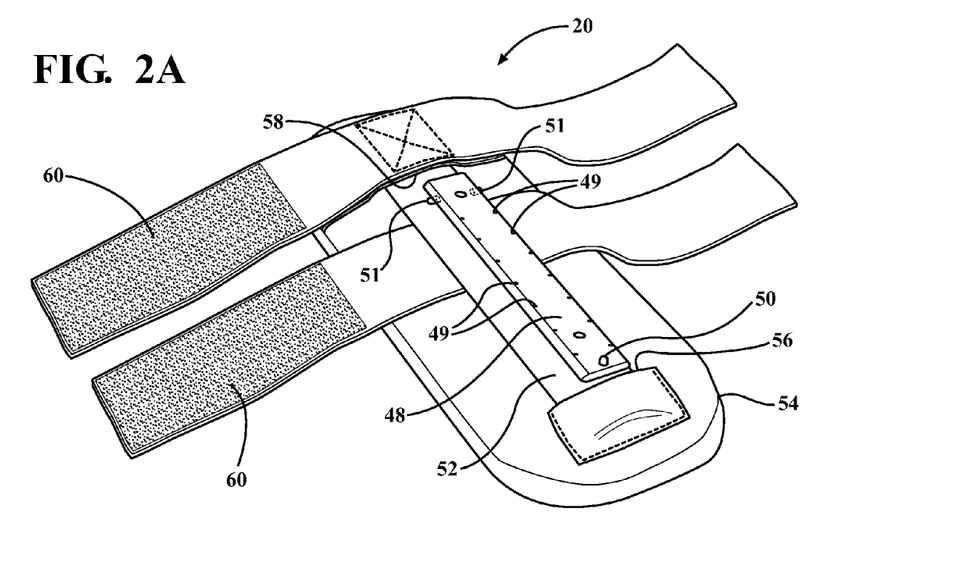
FIG. 2A is a bottom view of an arm support member of the surgical table arm support assembly of FIG. 1.
Figure 2B:
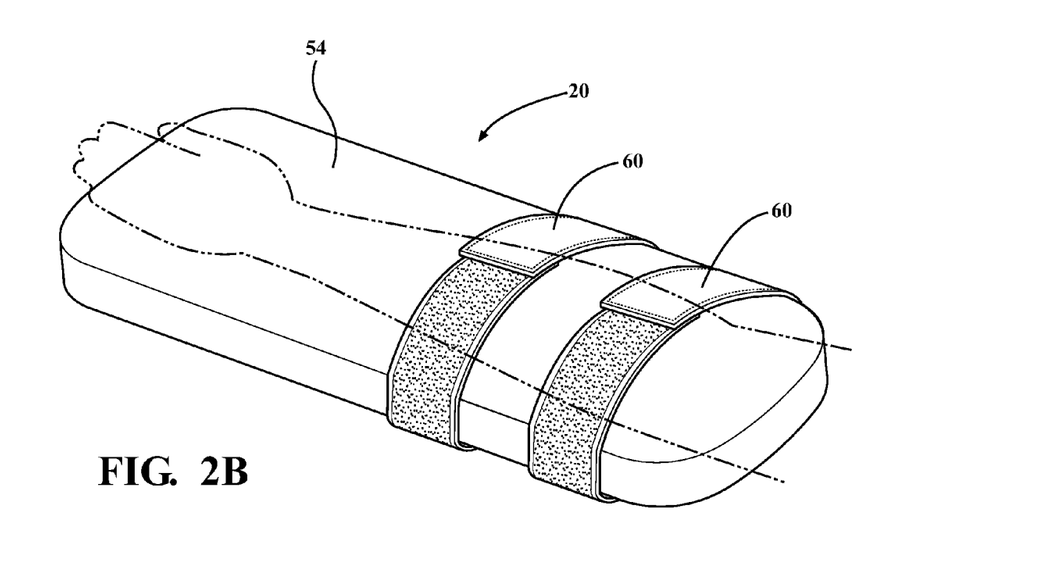
FIG. 2B is a top view of the arm support member of FIG. 2 with a patient's arm releasably secured thereto.
Figure 3:
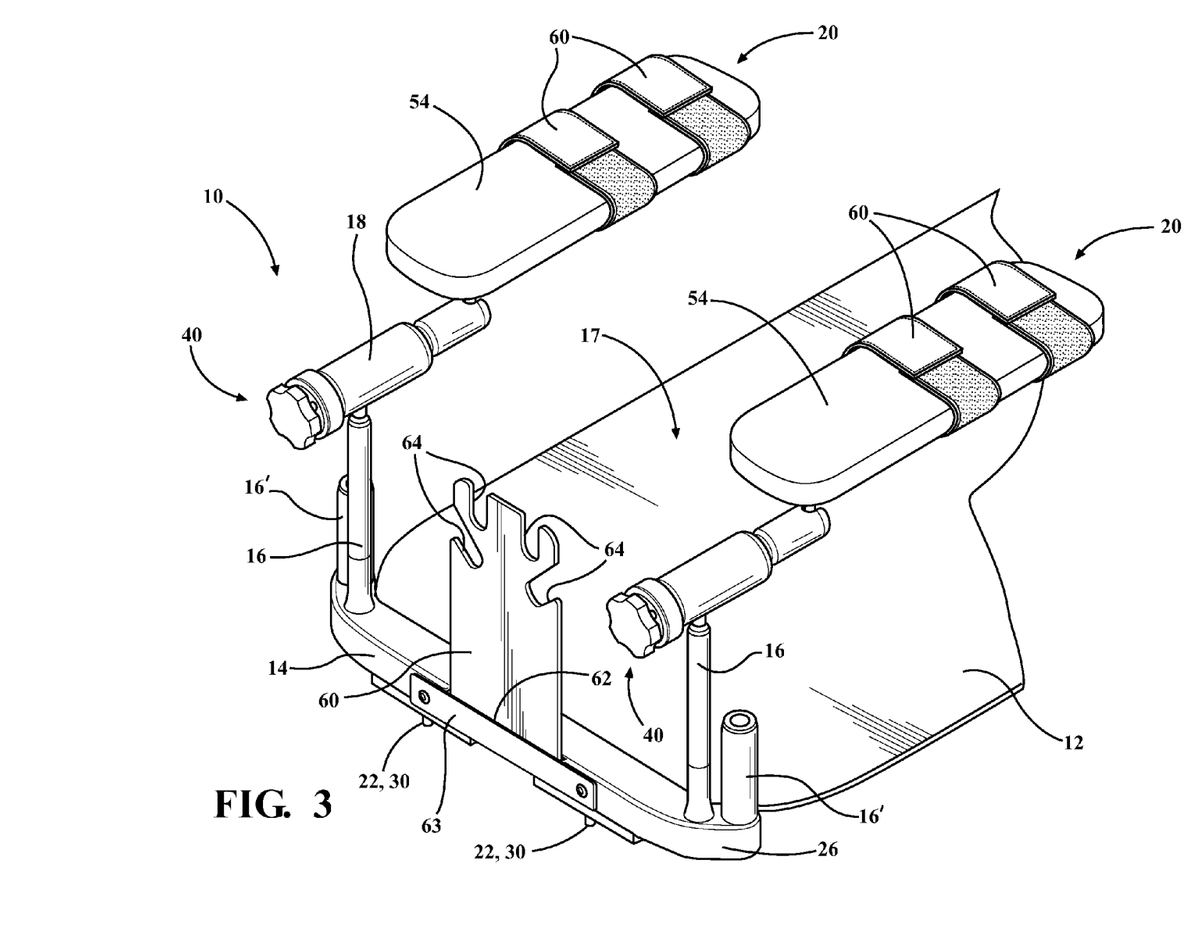
FIG. 3 is a partial perspective view of a surgical table with a pair of the surgical table arm support assemblies shown ready attached thereto and ready for use.
Figure 4:
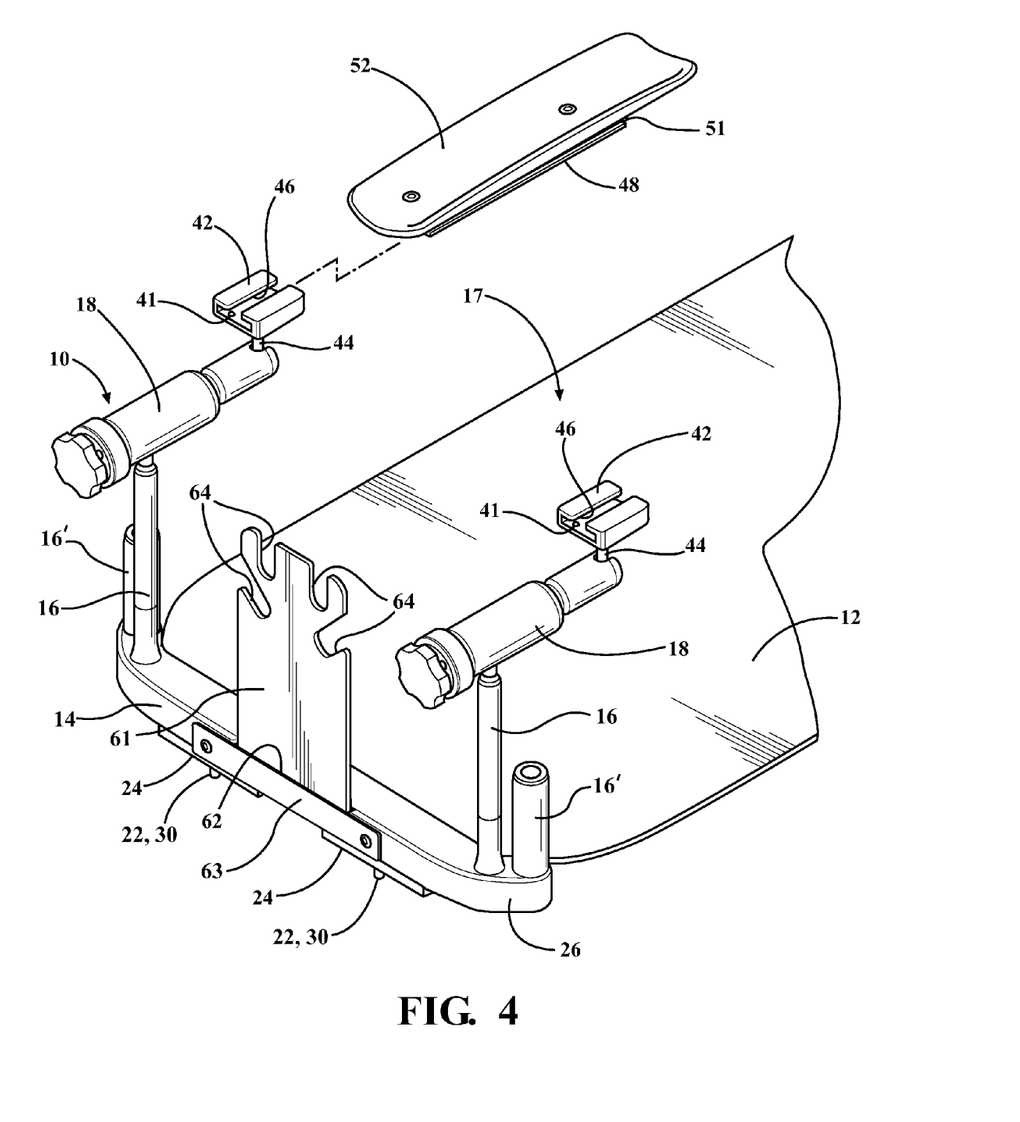
FIG. 4 is a view similar to FIG. 3 showing an arm support member, with a compliant arm pad removed therefrom, exploded from a lateral support member of one of the surgical table arm support assemblies.

Referring in more detail to the drawings, FIG. 1 illustrates a surgical table arm support assembly, referred to hereafter simply as assembly 10, constructed in accordance with one aspect of the invention, wherein the assembly 10 is shown operably and releasably attached to a surgical table 12. The assembly 10 includes a mount bracket 14 that enables quick attachment of the assembly 10 to the surgical table 12 and quick removal of the assembly 10 from the table 12, wherein the assembly 10 is shown here as being attached to one end of the surgical table 12. The assembly 10 further includes an upright support member 16 operably attached to the mount bracket 14, wherein the upright support member extends upwardly from a support surface 17 of the surgical table 12. The assembly 10 further includes a lateral support member 18 operably attached to the upright support member 16, wherein the lateral support member 18 extends generally laterally from the upright support member 16 in generally parallel relation with the support surface 17 of the surgical table 12. The lateral support member 18 is selectively movable about 3 axes (x, y, z) relative to the upright support member 16, and thus, it should be recognized that relative angles of inclination can be established between the lateral support member 18 and the support surface of the surgical table 12. The assembly 10 further includes an arm support member 20 operably attached to the lateral support member 18, wherein the arm support member 20 extends generally laterally away from the upright support member 16 in cantilevered fashion from the lateral support member 18 and is selectively movable about 3 axes (x, y, z) relative to the lateral support member 18, thereby allowing the arm support member 20 to be swiveled and positioned as desired. Accordingly, the arm support member 20 can be precisely positioned and releasably fixed in space to enable the patient's arm to be properly and precisely positioned to best prevent trauma to the patient's brachial plexus, even while the patient's arm is supported for an extended period of time (hours) in a rearward facing, raised orientation, as shown in FIG. 1.

Figure 5:
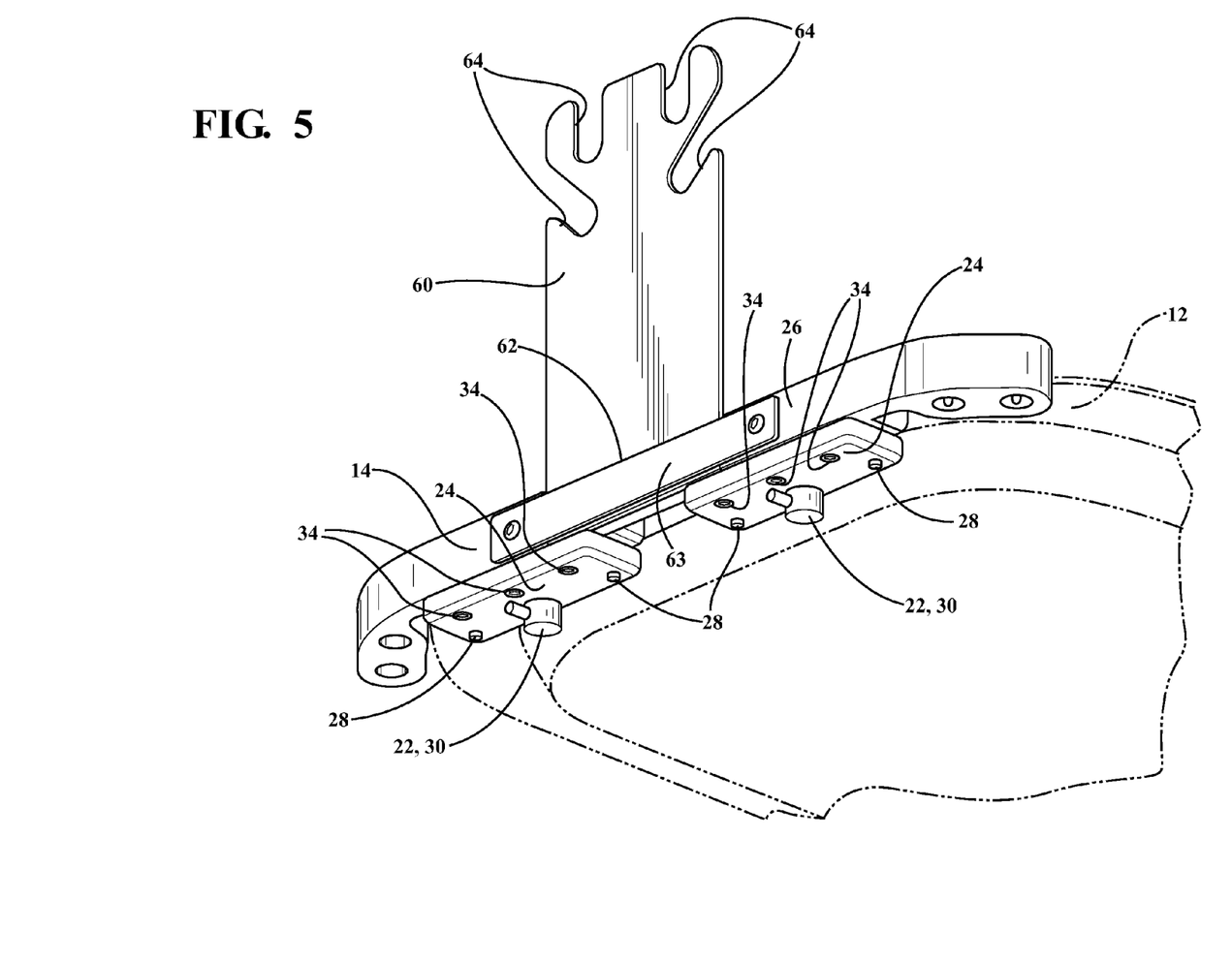
FIG. 5 is a partial perspective view of a surgical table showing a mount bracket and line guide releasably attached to the surgical table arm support assembly of FIG. 1.

The mount bracket 14, as best shown in FIG. 5, has at least one, and shown has a pair of fasteners 22 for quickly attaching the support 10 to the surgical table 12 and removing the support 10 from the surgical table 12. The fasteners 22, by way of example and without limitation, are each threaded through an opening in a separate base plate 24, wherein the base plates 24 are fixed to a main body 26 of the bracket 14 via fasteners 28. The fasteners 22 have hand-actuatable knobs 30 at one end and a clamp member (not shown) fixed on an opposite end. The ends of the fasteners 22 attached to the clamp members are freely rotatable within the clamp members, thereby allowing relative rotation therebetween. As such, when the knobs 30 are rotated in a first tightening direction, the clamp members move away from the base plates 24 toward the main body 26, wherein a portion of the surgical table 14 that is disposed between the clamp members and the main body 26 is fixedly clamped therebetween (such as in a standard vise clamp). To facilitate movement of the clamp members, the clamp members are preferably guided along one of more guide rods 34 extending between base plates 24 and the main body 26. Of course, when the knobs 30 are rotated in a second loosening direction, the clamp members move away from the main body 26, wherein the surgical table 12 is freely released from being clamped between the clamp members and the main body 26, and thus, the support 10 can be quickly and readily removed from the surgical table 12.

The upright support member 16 can be provided having any desired length. To enable different heights to be readily attained, the upright support members 16 are configured for stackable receipt of any number of extensions 16', wherein the extensions 16' can be stowed on the mount bracket 14 and used when desired, as shown in FIG. 1. Accordingly, it should be recognized that any desired height can be quickly attained by simply using the desired number of extensions 16' in combination with the upright support 16. Of course, the support members 16 can be used without use of the extensions 16' if the support member 16 is the height desired by the surgeon.

Figure 8A:
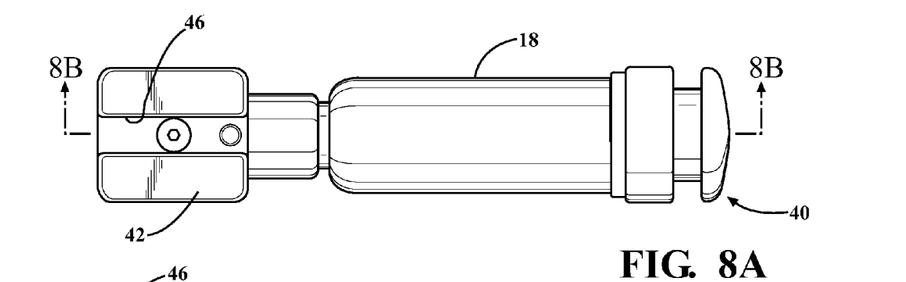
FIG. 8A is a top view of a lateral support member and the upright support member of the surgical table arm support assembly of FIG. 1.
Figure 8B:
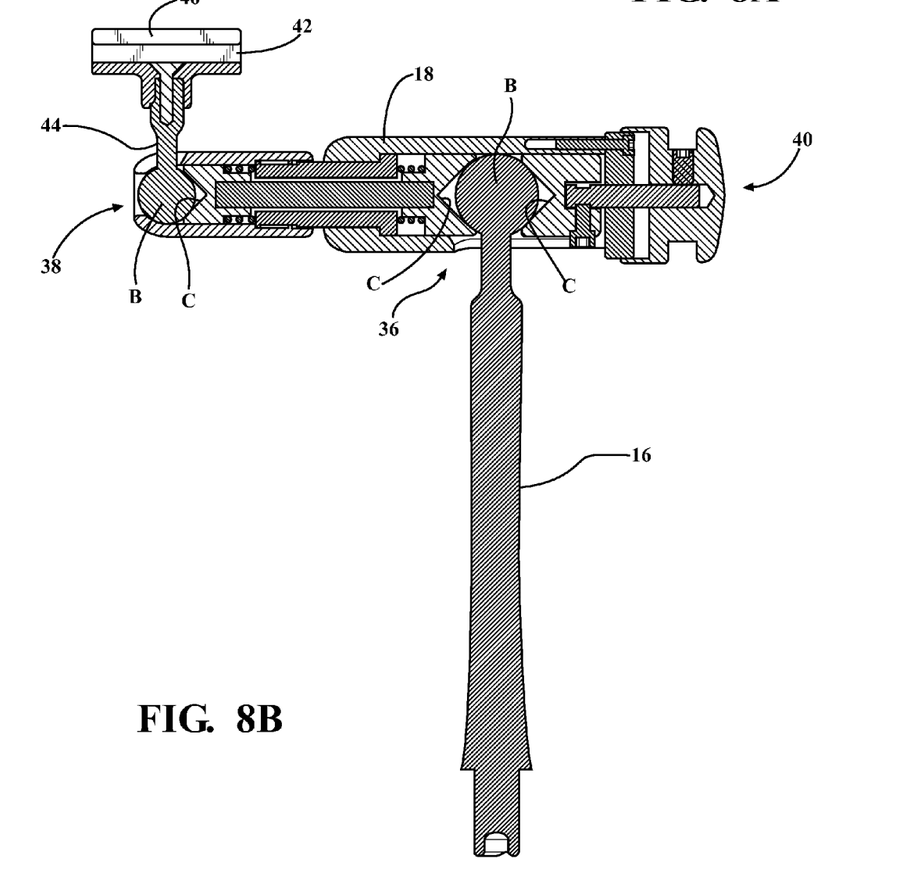
FIG. 8B is a cross-sectional view taken generally along the line 8B-8B of FIG. 8A.

As shown in FIG. 8B, the lateral support members 18 are operably coupled to the upright support members 16 for 3-axes (x, y, z) pivotal movement thereon, and the arm support members 20 are operably coupled to the upright support members 16 for 3-axes (x, y, z) pivotal movement thereon, and thus, they both have individual, full 3-axes degree movement. The upright support member 16 and lateral support member 18 are coupled to one another via a selectively lockable first ball joint 36 and the lateral support member 18 and arm support member 20 are operably couple to one another via a selectively lockable second ball joint 38. The first and second ball joints 36, 38 are selectively lockable and unlockable simultaneously via a single quick lock and release member 40. The quick lock and release member 40 needs only to be rotated about 90 degrees to fully unlock the first and second ball joints 36, 38 to allow full freedom of movement of both the lateral support member 18 and the arm support member 20 for individual 3-axes adjustment of both the lateral support member 18 and the arm support member 20, whereupon the quick lock and release member 40 can be rotated back approximately 90 degrees to its locked position to fix the horizontal support member 18 and the arm support member 20 in their selected positions. As shown in FIG. 8B, it will be readily understood by one possessing ordinary skill in the art that the rotation of the quick lock and release member 40 causes cam surfaces C to be moved into locking engagement and unlocking disengagement with the balls B of the ball joints 36, 38. Accordingly, the ability to position and reposition the patient's arm prior to and during the procedure is made quick, precise and easy via the quick lock and release members 40.

The arm support member 20 is releasably coupled to the lateral support members via a mount plate 42. The mount plate 42 is supported by a stud 44 of the second ball joint 38. The mount plate 42 has a receptacle, shown as a slot 46, configured for releasable, sliding attachment to a mating member 48 of the arm support member 20. The slot 46 and mating member 48 can be configured having a dovetail type configuration, by way of example and without limitation. To ensure the arm support member 20 remains fixed to the mount plate 42, a spring actuated detent 50 can be provided at one end of the mating member 48, by way of example, and a rib or ribs 51 can be provided at an opposite end of the mating member 48, wherein the spring detent 50 is automatically biased by a spring to an outwardly extended locked position and can be readily depresses inwardly against the bias of the spring to an unlocked position, when desired. As such, the arm support member 20 can be readily removed from the mount plate 42 when desired by simply depressing the spring detent 50 sufficiently to move it to its unlocked position and then sliding the arm support member 20 off the mount plate 42. It should be recognized that the arm support member 20 is slidably, telescopically adjustable while fixed on the mount plate 42, and can be releasably maintained in its desired position via snapping, ratcheting interaction of raised protrusions or bumps on one of the members, such as a raised bump 41 on an inner surface of the mount plate 42 with corresponding depressions in the other of the members, shown as a plurality of depressions or recessed pockets 49 on the mating member 48. It should be recognized that when a protrusion 41 is received in the selected recessed pocket 49, the arm support member 20 is generally fixed in its desired location; however, a sufficient manually applied force can be selectively applied to the arm support member 20 to move the protrusion 41 out of the recessed pocket 49, when desired. If the protrusion 41 is disengaged from the recessed pocket 49, the arm support member 20 can be telescopically adjusted to a position either extended further away from the lateral support member 18 or retracted toward the lateral support member 18, whereupon the protrusion 41 can be ratcheted into a different recessed pocket 49 to releasably maintain the arm support member 29 in its new position. While adjusting the arm support member 20 telescopically, the detent 50 and the ribs 51 prevent the arm support member 20 from being inadvertently removed from the mount plate 42 by interfering with an end of the mount plate 42, thereby acting as a safety mechanism against inadvertent removal. Only when the detent 50 is purposely depressed inwardly can the arm support member 20 be removed from the mount plate 42. Accordingly, the arm support member 20 is not only pivotal relative to the lateral support member 18, but the arm support member 20 can also translate linearly toward or away from the lateral support member 18, thereby enhancing the ability to precisely adjust the position of the arm support member 20. Further, as discussed above, the arm support member 20 can be intentionally removed and separated from the mount plate 42, and thus the lateral support member 18, simply by depressing the spring detent 50 and sliding the arm support member 20 off the mount plate 42, if desired.

Figure 6A:
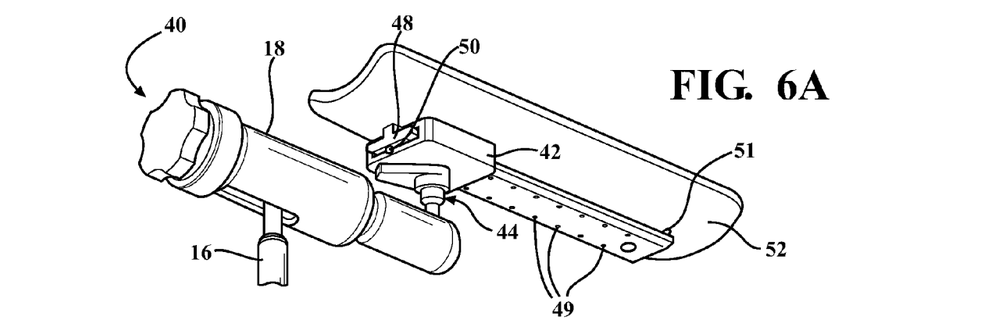
FIGS. 6A-6C show bottom perspective views of differently sized arm support members of the surgical table arm support assembly of FIG. 1.
Figure 6B:
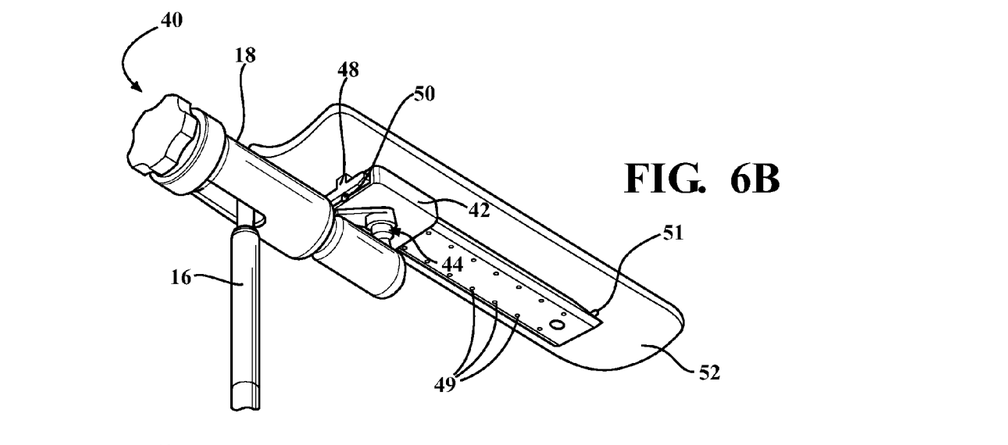
Figure 6C:
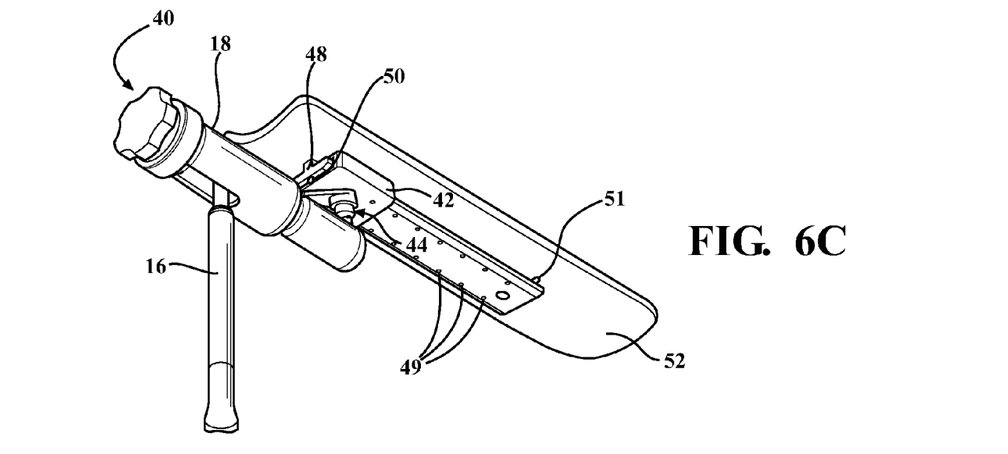
Figure 7A:
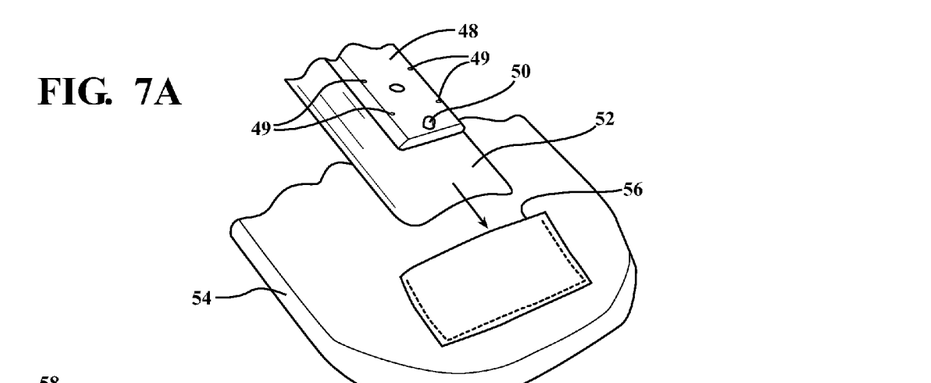
FIG. 7A shows a first end of a rigid support plate of the arm support member being inserted into a pocket of a compliant arm pad of the surgical table arm support assembly of FIG. 1.
Figures 7B, 7C:
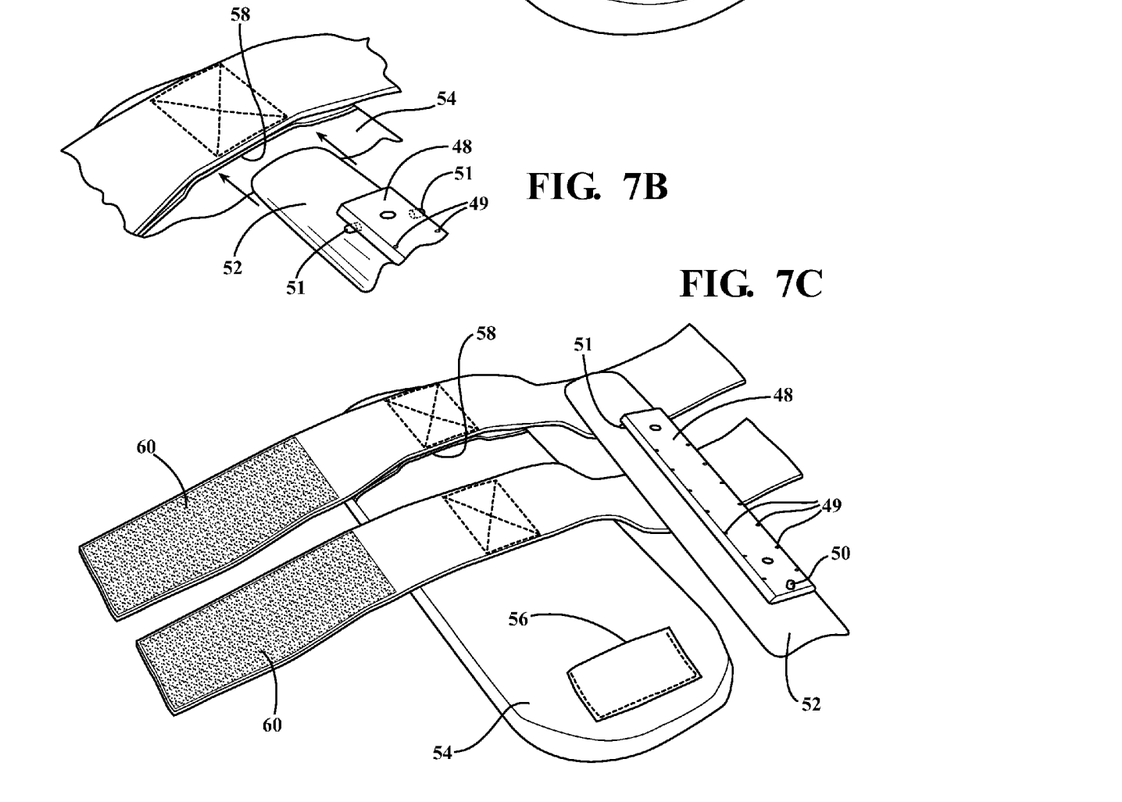
FIG. 7B shows a second end of the rigid support plate of the arm support member inserted into another pocket of the compliant arm pad.
FIG. 7C shows the compliant arm pad detached from the rigid support plate of the arm support member.

The arm support member 20, as best shown in FIGS. 2A, 2B and 7A-7C, includes a rigid support plate 52 and a compliant arm pad 54 releasably fixed to the rigid support plate 52. The mating member 48 is shown as being fixed to a bottom surface of the support plate 52, and the arm pad 54 is shown as being releasably attached to the support plate 52. It should be recognized that the mating member 48 and the support plate 52 can be formed as a singled piece of material, such as via molding, by way of example and without limitation. The arm pad 54 is shown as having pockets 56, 58 at opposite ends thereof, wherein the pockets 56, 58 are sized for close, slidable receipt of opposite ends of the support plate 52. To facilitate releasably fixing the patient's arm to the arm pad 54, the arm pad 54 is preferably provided with one or more straps 60, shown as having a hook and loop (Velcro) type fastening mechanism, by way of example and without limitation, for quick release and fastening of the patients arm to the compliant arm pad 54. As shown in FIGS. 6A-6C, the rigid support plate 52 can be provided having any desired size, such as would be suitable for infants (FIG. 6A), adolescents (FIG. 6B) and adults (FIG. 6C), wherein it is to be understood that the arm pad 54 would be provided to conform with the size of the support plate 52.

The support 10 can further include a line guide member 61 operably attached to the mount bracket 14, such as via any suitable fastener or fasteners, or by sliding receipt of an end of the line guide member 61 into a slot or receptacle 62 of the mount bracket 14, wherein the pocket 62 is shown as being formed between a plate 63 and a recessed slot formed in the mount bracket 14, by way of example and without limitation, wherein the plate 63 is shown fixed to the mount bracket 14 via any suitable fastener or bond joint. As such, the line guide member 61 can simply be disposed and removed from the pocket 62, as desired. The line guide member 61 has a plurality of line support regions 64, show as generally U-shaped notches or slots, sized for receipt of lines, e.g. wires, catheters, tubing, and the like, therein, for releasably retaining lines in a fixed or substantially fixed position. Accordingly, the surgical team can organize and route lines as desired to avoid having them causing an obstruction or otherwise becoming a nuisance and presenting a potential danger during the surgical procedure. To facilitate being able to image the patient through the line guide member 61, the line guide member 61 can be constructed from a radiolucent material, such as carbon fiber, by way of example and without limitation.

The compliant arm pad 54 can be provided from any desired compliant material, such as foam, rubber, and the like, and further, can be provided as a thermo-formable material to facilitate forming the pad 54 having a contoured shape to provide optimal comfort to the patient. Regardless of the compliant material used, the arm pad 54 can be provided having an outer shell or layer that can be readily wiped clean and sterilized, such as an impervious layer of polymeric material, by way of example and without limitation.

In use, the support 10 is readily attachable and removable from the standard surgical table 12 via the clamp member of the mount bracket 14. Upon attaching the mount bracket 14 to the surgical table 12, the suitable height upright support member 16 with lateral support member 18 coupled thereto, and optionally upright support extension 16', can be attached to the mount bracket 14. Then, the desired size arm support member 20 can be readily attached to horizontal support member 18. Then, with the support 10 being fixed to the surgical table 12, the quick lock and release member 40 can be moved to the release or unlock position whereupon the lateral support member 18 and arm support member 20 can be freely pivoted and manipulated via the respective ball joints 36, 38 to bring the arm support member 20 into the precise and desired location to best support the patient's arm and minimize the risk of trauma to the patient's brachial plexus. To further facilitate bringing the arm support member 20 into its optimal position, the arm support member 20 can be translated telescopically relative to the lateral support member 18, either toward or away from the lateral support member 18 via ratcheting interaction of the protrusion 41 with the recessed pockets 49, as discussed above. To further facilitate performing the surgical procedure, the lines being used can be routed through one or more of the support regions 64 of the line guide member 61. Of course, if readjustment of the patient's arm is desired, the arm support member 20 can be readily readjusted via unlocking the quick release lock member 40; repositioning the arm support member 20, and then relocking the quick release lock member 40. Further, if desired, the support 10 can be easily remove from the surgical table 12 by simply loosening the fasteners 22 and pulling the support from the table 12. After use, the support 10 can be readily sterilized for future use.

Many modifications and variations of the present invention are possible in light of the above teachings. It is, therefore, to be understood that the invention may be practiced otherwise than as specifically described, and that the scope of the invention is defined by any ultimately allowed claims.

What is claimed is:

1. A surgical table arm support assembly, comprising:
   a mount bracket configured for attachment to a surgical table;
   an upright support member operably attached to said mount bracket;
   a lateral support member operably attached to said upright support member, said lateral support member being movable about 3 axes relative to said upright support member; and
   an arm support member operably attached to said lateral support member, said arm support member being movable about 3 axes;
   wherein said arm support member includes a rigid support plate and a compliant arm pad releasably attached to said rigid support plate;
   wherein said lateral support member has a mount plate for releasable attachment of said arm support member thereto; and
   wherein said mount plate has one of protrusions and or recessed pockets and said rigid support plate has the other of said protrusions or recessed pockets, said recessed pockets being aligned to slidingly receive said protrusions in ratcheting fashion toward or away from said lateral support member to selectively maintain said arm support in a releasably fixed position.

2. The surgical table arm support assembly of claim 1, further comprising a single lever operable to simultaneously lock said lateral support member, said arm support member, and said upright support member against relative movement with one another, and to simultaneously release said lateral support member, said arm support member, and said upright support member for relative movement with one another.

3. The surgical table arm support assembly of claim 1 wherein said arm support member is slidably moveable relative to said lateral support member.

4. The surgical table arm support assembly of claim 1 further including a line guide member operably attached to said mount bracket, said line guide member having a plurality of line support regions for releasably retaining lines in a fixed position.

5. The surgical table arm support assembly of claim 1, wherein said mount bracket further comprises:
   a pair of fasteners to attach said mount bracket to said surgical table, wherein said pair of fasteners is rotatable in a first tightening direction to secure said mount bracket to said surgical table, and wherein said pair of fasteners is rotatable in a second loosening direction to free said mount bracket from said surgical table.

6. The surgical table arm support assembly of claim 1, wherein said mount bracket further comprises:
   a main body;
   at least one base plate; and
   at least one fastener rotatably configured to move said at least one base plate toward and away from said main body.

7. The surgical table arm support assembly of claim 6, wherein said surgical table is secured between said main body and said at least one base plate.

8. The surgical table arm support assembly of claim 1, further comprising:
   at least one vertical extension configured for stackable receipt on said mount bracket, wherein said upright support member is supported by said at least one vertical extension.

9. The surgical table arm support assembly of claim 3, further comprising a spring-actuated detent between said lateral support member and the arm support member for sliding said arm support member about said lateral support member.

10. In combination, a surgical table arm support assembly and surgical table having an upper patient support surface, said surgical table arm support assembly, comprising:
    a mount bracket operably attached to said surgical table;
    an upright support member operably attached to said mount bracket, said upright support member extending upwardly from said upper patient support surface of said surgical table;
    a lateral support member operably attached to said upright support member about a ball joint, said lateral support member extending laterally from said upright support member and being movable about said ball joint about 3 axes; and
    an arm support member operably attached to said lateral support member in cantilevered relation with said lateral support member, said arm support member extending laterally away from said upright support member and being movable about 3 axes;
    wherein said arm support member includes a rigid support plate and a compliant arm pad releasably attached to said rigid support plate;
    wherein said lateral support member has a mount plate configured for sliding receipt of said rigid support plate of said arm support member thereto; and
    wherein said mount plate has one of protrusions or recessed pockets and said rigid support plate has the other of said protrusions or recessed pockets, said recessed pockets being aligned to receive said protrusions in ratcheting fashion toward or away from the lateral support member to selectively maintain said arm support in a releasably fixed position.

11. The combination of claim 10, wherein said surgical table arm support assembly further includes a single lever operable to simultaneously lock said lateral support member, said arm support member, and said upright support member against relative movement with one another, and to simultaneously release said lateral support member, said arm support member, and said upright support member for relative movement with one another.

12. The combination of claim 10, wherein said surgical table arm support assembly further includes a line guide member operably attached to said mount bracket, said line guide member having a plurality of slots for releasably retaining lines in a fixed position.

13. The combination of claim 12, wherein said line guide member is radiolucent.

14. The combination of claim 10, wherein said arm support member is telescopically moveable relative to said lateral support member.

\* \* \* \* \*